Figure 3:
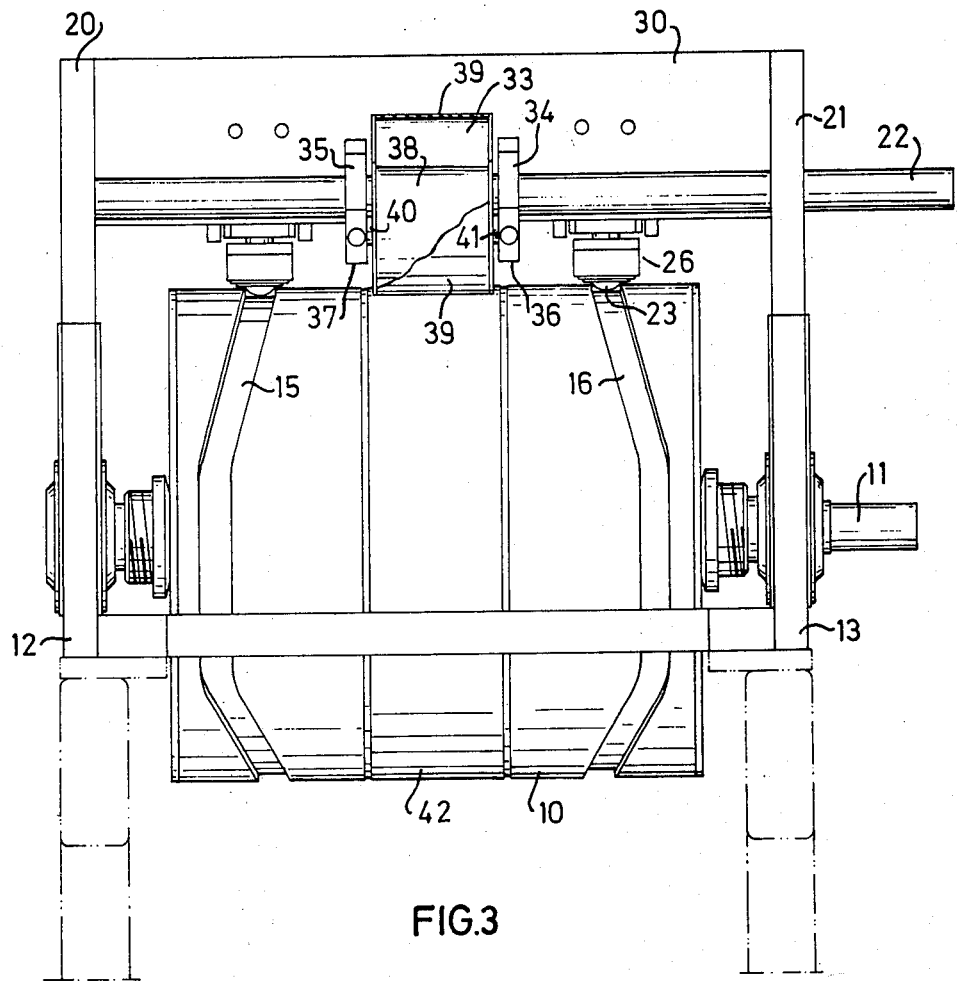

United States Patent [19]

Edling

[11] 4,273,014
[45] Jun. 16, 1981

[54] DEVICE FOR CUTTING OUT BLANKS FROM A WEB OF MATERIAL

[75] Inventor: Ernst G. S. Edling, Mölnlycke, Sweden

[73] Assignee: Mölnlycke AB, Goteborg, Sweden

[21] Appl. No.: 41,181

[22] Filed: May 21, 1979

[30] Foreign Application Priority Data

May 25, 1978 [SE] Sweden ............................ 7805988

[51] Int. Cl.³ ................................... B26D 1/28
[52] U.S. Cl. ............................. 83/333; 83/343; 83/422; 83/428; 83/430; 83/673
[58] Field of Search .................. 83/56, 428, 431, 509, 83/510, 495, 504, 333, 346, 659, 658, 331, 343, 422, 425.4, 430, 505, 586; 93/58.2 R, 58.1

[56] References Cited

U.S. PATENT DOCUMENTS

| 176,809 | 5/1876 | Randall | 83/333 X |
|---|---|---|---|
| 558,883 | 4/1896 | Walton | 83/343 X |
| 3,073,196 | 1/1963 | Marcalus | 83/659 X |
| 3,096,015 | 7/1963 | Bradbury | 83/685 X |
| 3,299,761 | 1/1967 | Goldman | 83/685 X |
| 3,787,968 | 1/1974 | Littmann | 83/510 X |
| 3,996,828 | 12/1976 | Granger et al. | 83/500 |
| 4,046,043 | 9/1977 | Kistner et al. | 83/430 X |
| 4,123,956 | 11/1978 | Harvey | 83/685 X |
| 4,168,643 | 9/1979 | Takimoto et al. | 83/430 X |

FOREIGN PATENT DOCUMENTS 2052836 4/1971 France .

Primary Examiner—Frank T. Yost
Attorney, Agent, or Firm—Young & Thompson

[57] ABSTRACT

A method and a device for cutting out pieces of material webs, the cutting taking place between a spherical surface and a sharp edge. The spherical surface consists of a freely movable, non-driven ball. The ball can be made of hard material such as steel and the cutting edge of softer material, or vice versa. The device consists of a roller over which the web is led and a member acting against it. The roller has a groove corresponding to the desired contours of the formed piece. A ball, guided by the groove made in the roller, presses against the edge of the groove for cutting through the web.

4 Claims, 3 Drawing Figures

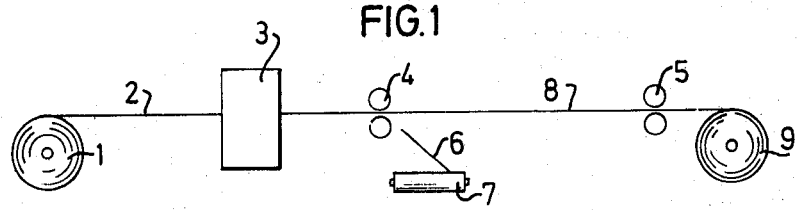
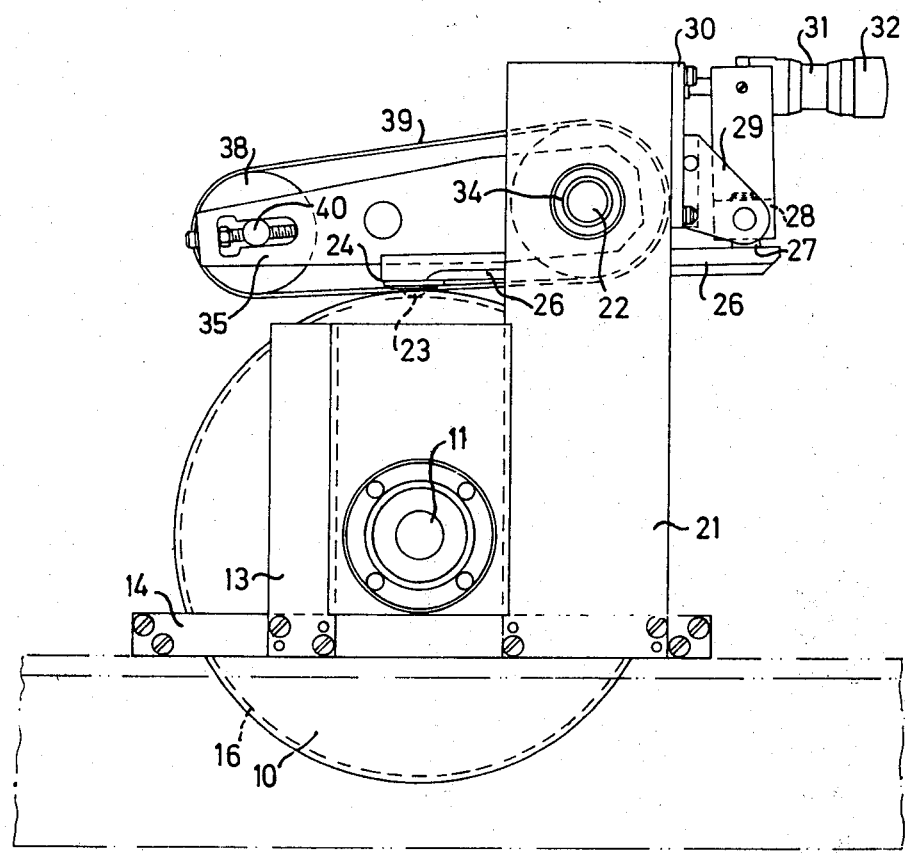

DEVICE FOR CUTTING OUT BLANKS FROM A WEB OF MATERIAL

For producing blanks in large series inexpensively and rapidly, there is a rich selection of devices and methods, depending on the starting material and its characteristics. Entirely different devices and process are used, of course, for stamping sheet metal blanks, paper figures, cloth blanks, dough, rubber sheets etc. For certain materials such as cloth in the clothing industry, the material is laid in multiple layers and a number of blanks are cut out at the same time with a band saw, for example.

In the present case we are working with thin, preferably plastic/non-woven laminates, or solely non-woven material or solely plastic, from which blanks for diapers, incontinence products etc. are made. Sawing out blanks from multiple layers of this material can cause the blanks to stick together at the cut edges. Consequently, for such cuttings the thin web has been run through a pair of rollers, one of which is a smooth counter roller, and the other is provided with knives corresponding to the desired cut-out (the cutting roller). The disadvantages of this previously known process are that the knife edges must be of very high precision to cut through the plastic web correctly and in all places, and that this precision is also required of both rollers, which are usually manufactured by spark machining. A damaged knife edge can require expensive and time-consuming repairs. In order to obtain a satisfactory cut, the rollers must be powerfully journalled in a very strong and rigid frame, with the result that if a hard or large foreign object were to come in between the rollers, the consequences would be in effect catastrophic.

The present invention intends to achieve a simple, inexpensive and reliable device which makes possible a rapid cutting out of blanks from material webs without the disadvantages involved in previous devices.

This is achieved according to the invention by cutting a groove in the counter-roller corresponding to the contours of the desired pieces. A ball presses against the edges of this groove and the cutting of the web is effected between this ball and one or both edges of the groove. This provides a number of advantages. The groove in the roller can be cut without any special precision with ordinary tools. When the groove edge, i.e. the cutting edge, becomes dull it can be sharpened quite simply by circular grinding of the roller, which may even be possible with the roller in place. The ball is an ordinary ball bearing ball, a common, inexpensive part which can simply be replaced when worn. The entire ball holder is also a standard product which is used for roller tables, pallets and the like. If a foreign object or a thickening of the material web should be drawn into the machine, the entire loaded ball holder is lifted up without any damage to the apparatus. The contact pressure can be adjusted with a single compressed air cylinder and need not have the precision required in a roller journalled at both ends. In the present device only a single roller is required, which need not be especially well machined. The frame can thus be of simple construction without having to be especially rigid. The cutting speed is at least as high as with previously known devices. Cutting the material between an edge and a spherical surface produces a shear which improves the cutting result.

The invention will be described here in more detail in connection with the accompanying drawings, of which FIG. 1 shows schematically an example of an arrangement of the device according to the invention, FIG. 2 shows a longitudinal section through the device, and FIG. 3 shows the device as viewed from the front.

From a roll 1 of a thin material for manufacturing diapers or the like, a web 2 is drawn through the cutting device 3 according to the invention by two pairs of rollers 4 and 5. An edge cutting of the material is done in the cutting device 3 and roller pair 4 is disposed to cut up the edge-cut web into pieces of the desired length 6, which then fall down onto a conveyor for transport to further processing. The edge material, the waste, 8 is pulled forward by the roller pair 5 and is collected in a waste container 9 for recycling. The material usually consists of laminates of various compositions, for diapers, incontinence products or other hygiene products, but for other purposes the material can consist of polyvinyl chloride-vinyl acetate copolymers, polyvinylidene, polyethylene, polypropylene, solely non-woven material, etc. depending on the characteristics desired in the finished products. The invention is described in this example in connection with the cutting of plastic/non-woven laminates, but it has been able to be used with equally good results for paper, fibrous non-woven fabric, textile materials such as gauze, wire-reinforced plastic sheeting.

The cutting device 3 according to the invention is shown in more detail in FIGS. 2 and 3. A roller 10 is journalled with its shaft 11 in two bearing brackets 12 and 13, fixed in a frame (generally designated 14). The roller 10 is driven by a device which is not shown. Two grooves 15,16 are cut in around the roller 10, in a shape corresponding to the longitudinal edges of the finished blanks. The diameter of the roller is chosen at each occasion and for each product so that the circumference will be a multiple of the desired length of the finished blanks, so that if long pieces are being made, one or possibly two blanks can be cut from one revolution of the roller. For shorter pieces, the roller circumference can correspond to the length of three or more blanks, thus making the device quite flexible. There is, of course, the possibility of cutting endless webs in this manner.

The roller can be of very simple design, a tube with end pieces to which an axle is welded. The groove is then cut out with a shank-end mill. The width and depth of the groove need not be extremely precise. The edges of the groove can be sharpened additionally by grinding the roller, and resharpening after wear or damage can be easily done by regrinding the roller, possibly with the roller in place.

One of the edges of the groove can be bevelled, so that cutting is only done against the remaining sharp edge, if one wishes to avoid small pieces of waste material.

Two uprights 21 and 21 are fixed to the frame 14, which support to actual cutting members, and possibly an axle 22 for the auxiliary feed means.

The actual cutting is done with a ball 23 which presses the material web 1 against the groove edges, whereby the sharp groove edge cuts through the material. Two identical cutting members are arranged, one for each groove. The ball is mounted in a ball holder 24 of conventional type, of the same type as those used in roller tables, conveyors and the like, in which the ball is held securely in a ball socket, and is mounted against smaller balls, so that it moves easily even under load. The ball holder is fixed on an arm 26 which is pivotable laterally around a pin 27. The pin is journalled in a cross-piece 28 which is in turn fixed in a holder 29 mounted on a transverse beam 30 between the uprights 20 and 21. By applying a load to the upper end of the pin 27 with a compressed air cylinder 31, the contact pressure of the ball against the groove edge can be set to produce a satisfactory cut, depending on the thickness and toughness of the material and the sharpness of the cutting edge etc.

Because the arm 26 can be swung laterally, the ball can follow the groove even though its path meanders, and the resilience in the arm 26 prevents serious disturbances of operation due to thicker portions of the web, foreign objects etc.

As was mentioned above, two grooves and two cutting members are usually used to cut out pieces with two shaped edges. There is, however, nothing to prevent one from cutting out two pieces at the same time with one edge in each piece being the straight edge of the web. Likewise, several cutting members can be used to cut out several pieces at the same time.

In certain cases it may be so that the material cannot be fed satisfactorily over the counter roller, and additional control of the web is necessary to avoid stretching and deformation which can occur in certain materials. Gauze has proven to be especially difficult in this respect. For this purpose, on the axle 22 (which is driven in a manner not shown here synchronically with the counter roller 10) there is mounted a roller 33 midway between the two uprights 20 and 21, and two link arms 36 and 37 are mounted in bearings 34 and 35. These link arms support an additional roller 38 and a belt 39 passes around the two rollers, the under portion of the belt lying in contact with the counter roller. The center portion of the web will thus be guided between the drive belt 39 and the counter roller 10.

To set the tension and correct running of the belt, there is a tension device 40,41 for the roller 38 in the forward end of each link arm.

The required contact pressure between the belt 39 and the counter roller 10 is produced by the very weight of the roller 38 and the link arms 36,37. To improve the feed still further, the counter roller 10 can be made in different materials, and have a center portion 42 of a different material, for example a surface coating of rubber, a roughened surface etc.

The example has described the cutting of thin plastic/non-woven laminates.

What I claim is:

1. Device for cutting out formed pieces from thin web material, comprising a roller over which the web is led and means acting against the roller to press the web against the roller, characterized in that in the roller there is cut out a groove corresponding to the desired contours of the formed piece, the groove being disposed about the roller in a path whose position varies lengthwise of the rollers, and that a member is disposed to press against the edge of the groove and thereby cut through the material web, and means mounting said member for oscillatory movement lengthwise of said roller to follow said groove upon rotation of said roller.

2. Device according to claim 1, characterized in that the member is arranged to be guided by the groove cut into the roller.

3. Device according to claim 1, characterized in that the member is a ball.

4. Device according to claim 1, characterized in that said means is an endless belt that circulates with a speed equal to the peripheral speed of rotation of the roller thereby to advance the web between the belt and the roller.

* * * * *